US012667480B2

(12) United States Patent
Hsu

(10) Patent No.: US 12,667,480 B2
(45) Date of Patent: Jun. 30, 2026

(54) MANDIBLE DISPLACEMENT ADJUSTMENT DEVICE

(71) Applicant: Han-Chung Hsu, Taipei City (TW)

(72) Inventor: Han-Chung Hsu, Taipei City (TW)

( * ) Notice: Subject to any disclaimer, the term of this patent is extended or adjusted under 35 U.S.C. 154(b) by 627 days.

(21) Appl. No.: 18/009,282

(22) PCT Filed: Jun. 15, 2020

(86) PCT No.: PCT/CN2020/096159
§ 371 (c)(1),
(2) Date: Dec. 8, 2022

(87) PCT Pub. No.: WO2021/253174
PCT Pub. Date: Dec. 23, 2021

(65) Prior Publication Data
US 2023/0233360 A1     Jul. 27, 2023

(51) Int. Cl.
*A61F 5/56* (2006.01)
(52) U.S. Cl.
CPC .................................... *A61F 5/566* (2013.01)
(58) Field of Classification Search
CPC ......... A61F 5/56–566; A61F 2005/563; A61C 7/00–36; A63B 2071/086; A63B 2071/088
USPC ............................ 128/848, 859, 861; 433/24
See application file for complete search history.

(56) References Cited

U.S. PATENT DOCUMENTS 6,418,933 B1 *  7/2002  Strong .................... A61F 5/566
                                                    128/859
8,156,940 B2 *  4/2012  Lee ......................... A61F 5/566
                                                    128/848
2010/0263676 A1   10/2010  Thornton
2019/0105191 A1 *  4/2019  Sung ...................... A61C 7/002
2019/0175388 A1 *  6/2019  Urban ..................... A61F 5/566
2021/0236243 A1 *  8/2021  Liu ......................... G06F 18/22

FOREIGN PATENT DOCUMENTS

CN        208447894 U    2/2019
CN        110769789 A    2/2020
JP       2010509980 A    4/2010

* cited by examiner

*Primary Examiner* — Alireza Nia
*Assistant Examiner* — Robin Han
(74) *Attorney, Agent, or Firm* — LANWAY IPR SERVICES; Chun-Ming Shih

(57) ABSTRACT

A mandible displacement adjusting device includes an upper braces and a lower braces, wherein the upper braces and the lower braces have an upper teeth accommodation space and a lower teeth accommodation space, the upper teeth accommodation space and the lower teeth accommodation space are made based on the tooth shape, and fits on the upper and lower dental arches of the human body respectively, and the side walls of the upper braces and lower braces extend out a first positioning part and a second positioning part corresponding to the upper molar area and the lower molar area. When the user wear the upper braces and the lower braces, the first positioning part and the second positioning part would be driven to fit together, and maintain a movable displacement space, so that when the mandible of the human body is moved forward and fixed, it will not cause the mandible of the human body due to tightening, neither cause the discomfort at the condyle, while avoiding the back of the tongue slumping down and blocking the breathing passage.

7 Claims, 10 Drawing Sheets

MANDIBLE DISPLACEMENT ADJUSTMENT DEVICE

BACKGROUND OF THE INVENTION

1. Field of the Invention

The present invention relates to a mandible displacement adjusting device, in particular to a mandible displacement adjusting device which can make the mandible of the human body move forward to keep the breathing passage unobstructed, and solve the problems of apnea and snoring during sleep simultaneously.

2. Description of Related Art

There are many people who snore and stop breathing when sleeping. This is mainly because the muscles will relax during sleep, in addition, due to the relationship of gravity, as shown in FIG. 1, the support soft of oral cavity 101 inside mouth 10 will be the muscles of the palate and tongue root 7 fall down to squeeze the breathing passage 8, so that the air cannot be kept unobstructed and snoring will occur, and even more serious cases such as apnea or panting will occur. It is also called sleep apnea, and sleep apnea may affect sleep quality, and may even induce high blood pressure, heart disease and other diseases.

In order to solve the problems, there are many anti-snoring devices or anti-snoring devices on the market. Most of the existing anti-snoring devices use upper and lower braces and a connecting mechanism to move the mandible forward, to prevent the jaw from sagging and blocking the breathing passage 8.

However, the above-mentioned existing products all use a fixing mechanism to fix the upper and lower braces, because the mandible is forced to move forward, and the mandible cannot be moved back. However, if it is worn for a long time, it will cause the mandible condyle extremely sore, so the user will not be able to adapt to wearing this device, so it will be very troublesome for the user with respiratory arrest symptoms.

In addition, most of the existing anti-snoring devices are customized specifications, which do not conform to the shape of the user's dentition. There is a gap between the mouthpiece and the teeth, so there is a situation in which the position shifts or even falls off, which will prevent snoring and prevent The inefficiency of apnea occurs.

In addition, since the existing anti-snoring device is worn around the two rows of teeth of the maxilla and the mandible in the form of braces, the braces will have a certain thickness. If the mandible is moved forward, the thickness of the upper and lower braces themselves will make the occlusion of the incisor area produces an obvious foreign body sensation. If the user wears the device while sleeping, it will also make it difficult to fall asleep easily.

In addition, there is another anti-snoring device at present, which is to set the connecting mechanism at the incisor area, that is, by pulling the upper and lower incisors to force the mandible to move forward. However, this setting will make the incisor area stress, so under long-term wear, such a strong pull on the incisor area will cause the user to be extremely uncomfortable. That means this is not a type of device that can be used for a long time.

SUMMARY OF THE INVENTION

Therefore, in order to solve the above problems, the present invention is equipped with a first positioning part and a second positioning part at the upper and lower teeth, respectively, and an extension section and a hook are respectively extended from the upper and second positioning parts. After the hooks are hooked together, the mandible will be in the move forward position to keep the breathing passage 8 unobstructed, and solve the problems of apnea and snoring at the same time. In addition, because the upper and second positioning parts are not tight fit, but movable hooking, it has a full range of movement space to avoid the discomfort at the joints (condyle) of the mandible of the human body caused by fastening, so the present invention should be an optimal solution.

The present invention provides a mandible displacement adjustment device, comprising: an upper braces, having an upper teeth accommodation space, the upper teeth accommodation space is formed according to the shape of the teeth and used to fit on the maxilla of a human body, and side wall of the upper braces extends a first positioning part corresponding to an upper molar area, the first positioning part has a first extension part, and a front end of the first extension part has a first hook; a lower braces, having a lower teeth accommodation space, the lower teeth accommodation space is formed according to the shape of the teeth, and is used to fit on a mandibular dental arch of the human body, the mandibular dental arch is located in a mandible, and side wall of the lower braces extends out a second positioning part corresponding to a lower molar area, the second positioning part has a second extension part, and a front end of the second extension part has a second hook; wherein after the upper braces and the lower braces are worn, the first hook is driven to engage with the second hook, so that the mandible of the human body is moved forward and positioned, and the first extension part and the inner space of the first hook are an omnidirectional activity space for the second extension part and the second hook moving freely in the omnidirectional activity space, to let the mandible move freely relatively to avoid discomfort due to wearing at a condyle of the mandible for a long time.

In preferred embodiment, both the upper molar area and the lower molar area include a first premolar, a second premolar, a first molar, a second molar, and the positions of the first positioning part and the second positioning part can be corresponded to the side of either of the molars of the second molar and first molar, or between any two molars.

In preferred embodiment, the preferred positions of the first positioning part and the second positioning part correspond to the side of the first molar.

In preferred embodiment, the first positioning part is positioned on the position of the upper molar area, which is the preset position of this mandible forward positioning, the position of the first positioning part located in the upper molar area is tailored according to the acceptable position of the mandible forward positioning, so that the mandible will not generate discomfort when the mandible is positioned forward.

In preferred embodiment, the upper braces or/and the lower braces are provided with an opening corresponding to the front teeth area of the human maxillary dental arch or/and the human mandibular dental arch, so as to expose tooth surface of the front teeth area.

In preferred embodiment, the thickness of the upper braces and the lower braces relative to the front teeth area of the human maxillary dental arch and the human mandibular dental arch is less than 1 mm.

In preferred embodiment, the first positioning part and the second positioning part are a C-shaped or L-shaped structure that can be movably engaged.

In preferred embodiment, the second extension part of the second positioning part is blocked by the first extension part of the first positioning part and is unable to move backward at a blocking position when moving backward in the horizontal direction, and the blocking position is the preset position for mandible forward positioning.

In preferred embodiment, when the mouth of the human body is closed, the first hook of the first positioning part and the second hook of the second positioning part engage with each other, and when the mandible moves downward, the second hook will be blocked by the first hook to keep the mouth of the human body closed.

In preferred embodiment, wherein a first extension part of the first positioning part or a second extension part of the second positioning part can be set with an adjuster, the thickness of the adjuster is used to finely adjust the position of the mandible forward positioning.

In a preferred embodiment, a first extension part of the first positioning part or a second extension part of the second positioning part can be set with an adjuster, the thickness of the adjuster is used to finely adjust the position of the mandible forward positioning.

When the human body is sleeping, the mandible will move freely. If the mandible is fixed, after a long time, the condyle of the mandible will definitely produce great discomfort, and the present invention uses the first positioning part and the second positioning part. Both are C-type or L-type structures, so that the first extension part of the first positioning part and the inner space of the first hook form an omnidirectional activity space, for the second extension part of the second positioning part and the second hook can be in the omnidirectional activity space is free to move, so the mandible can move freely in all directions when the user is sleeping, and the condyle of the mandible will not cause any discomfort when wearing it for a long time.

When the mandible is moved forward and positioned, the tongue root and the support soft palate will be pulled upward at the same time to keep the breathing passage unobstructed, so as to solve the problems of breathing interruption and snoring caused by the user during sleep.

DETAILED DESCRIPTION OF THE INVENTION

Other technical contents, features and functions of the present invention will be clearly presented in the following detailed description of preferred embodiments with reference to the accompanying drawings.

Figure 1:
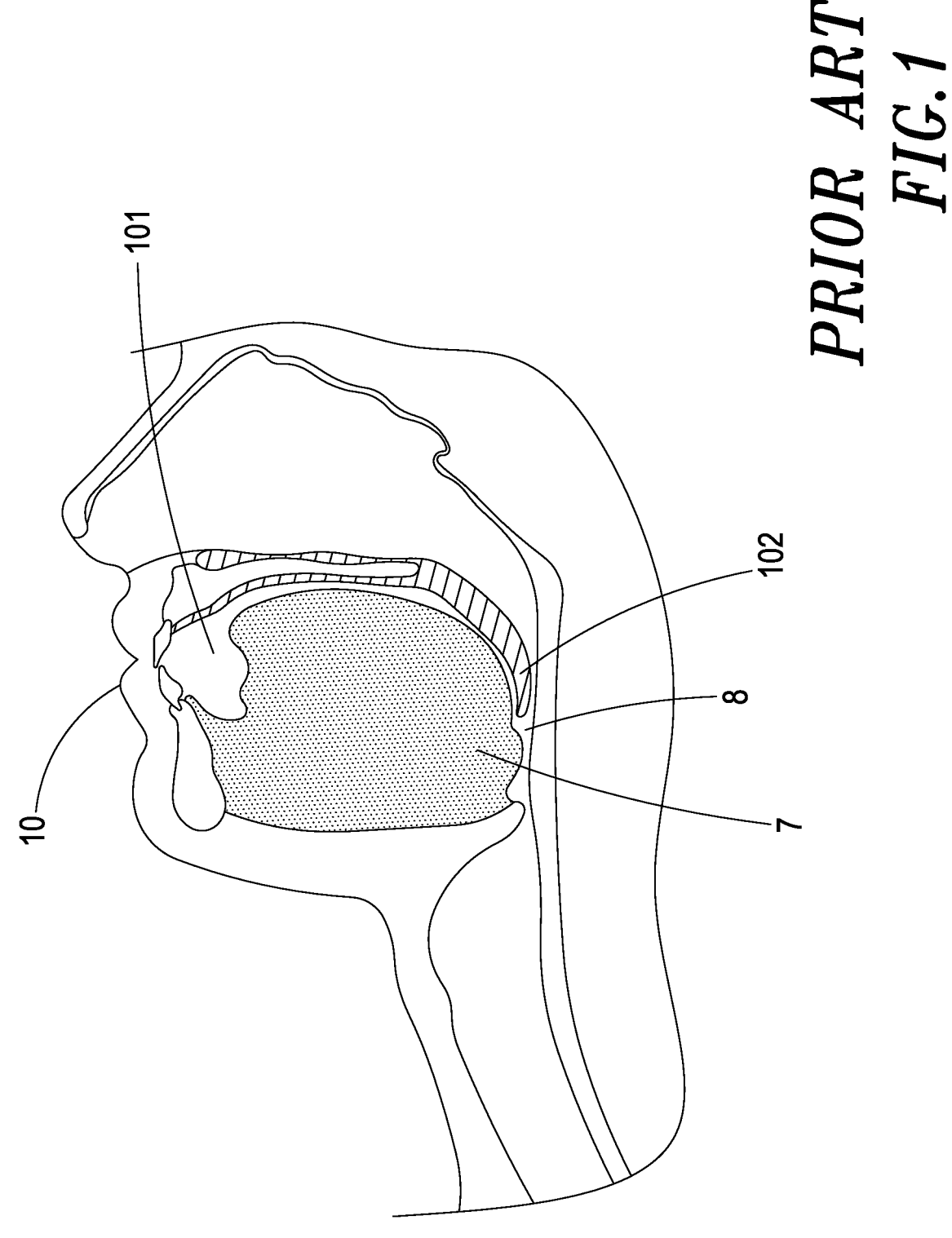
FIG. 1 is a schematic diagram of the muscles that are squeezed by the breathing passage of the human body.
Figure 2:
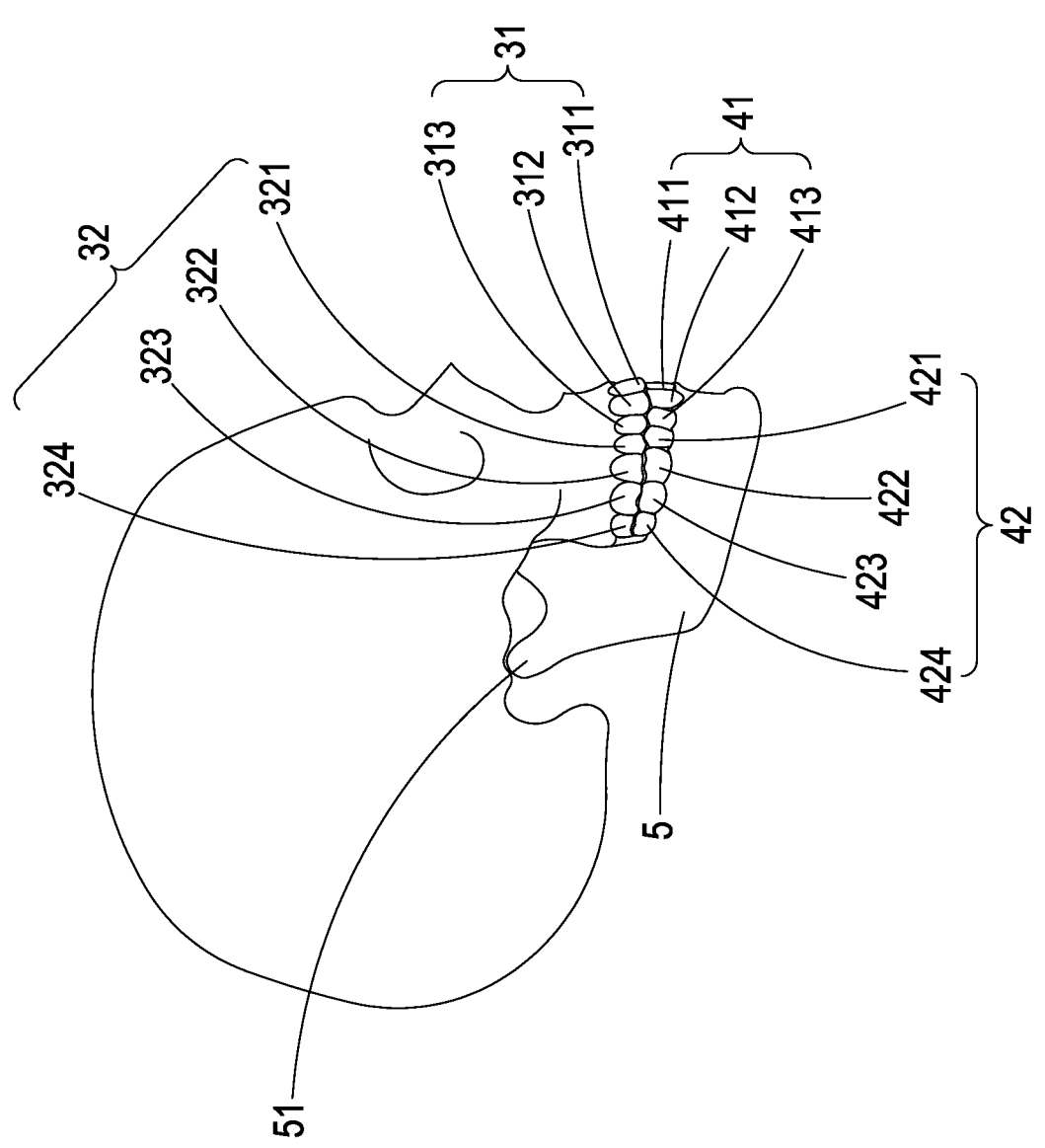
FIG. 2 is the dentition of human skull and mandible schematic diagram.
Figures 3A, 3B:
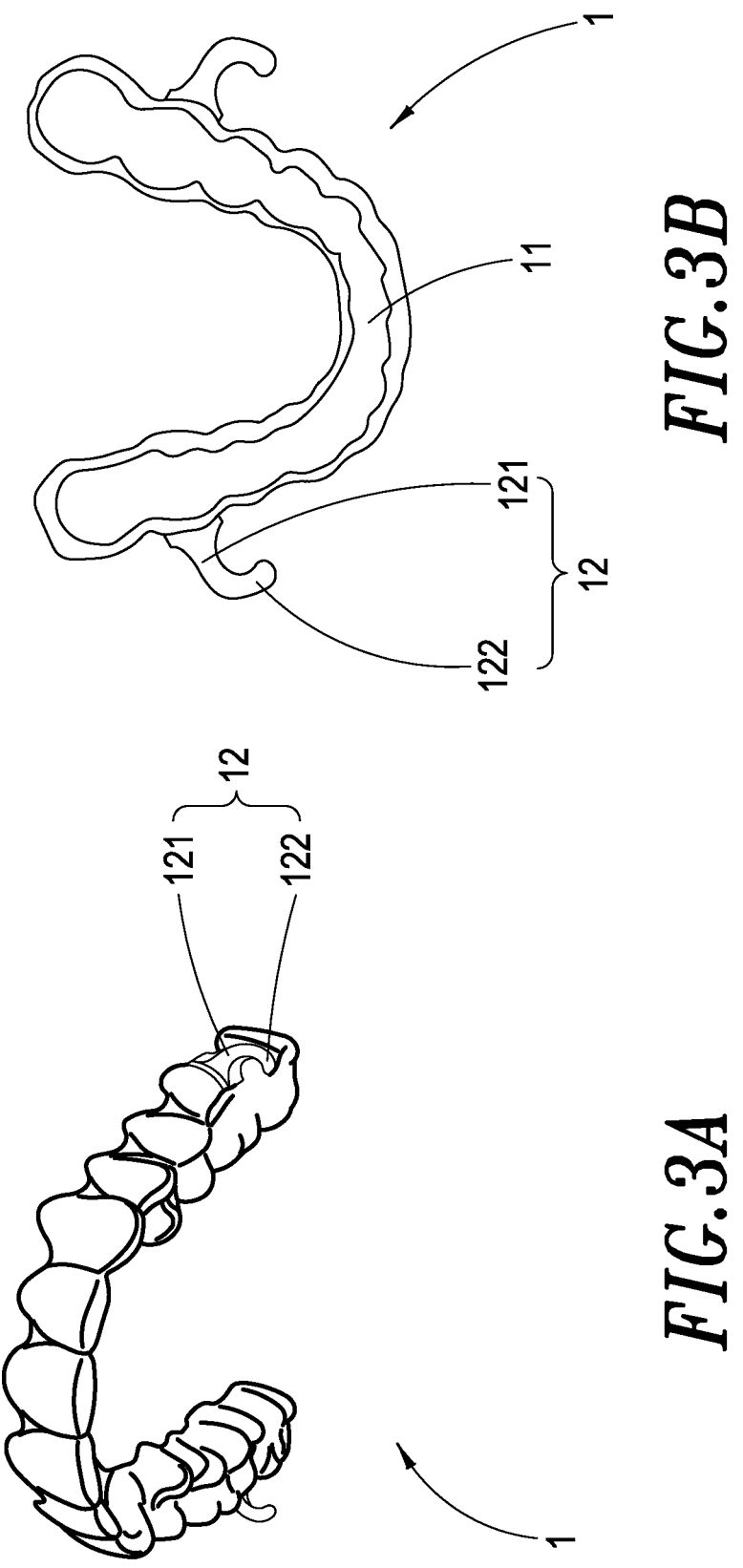
FIG. 3A is a schematic diagram of the three-dimensional structure of the upper braces of the mandible displacement adjusting device of the present invention.
FIG. 3B is a schematic top view of the upper braces of the mandible displacement adjusting device of the present invention.
Figure 4B:
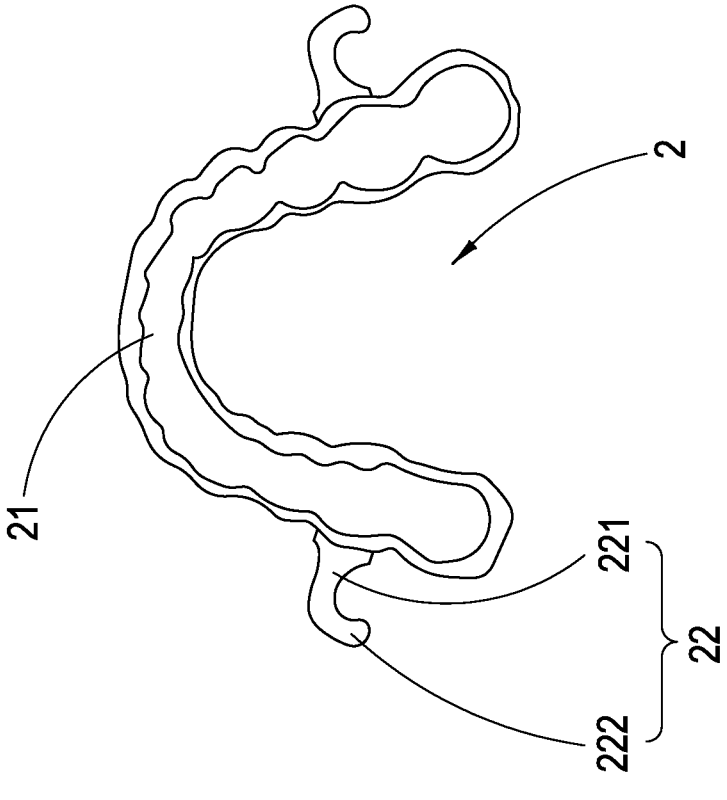
FIG. 4B is a schematic view of the lower braces bottom view structure of the mandible displacement adjusting device of the present invention.
Figure 4B:
Figure 4A:
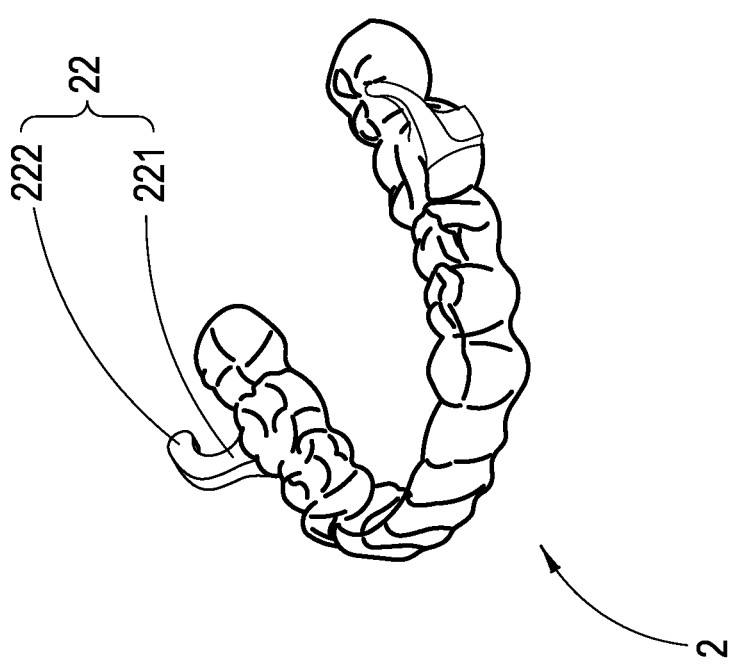
FIG. 4A is a schematic diagram of the three-dimensional structure of the lower braces of the mandible displacement adjusting device of the present invention.

As shown in FIG. 2, there are upper and lower dental arches in the human oral cavity, and the dentition of the upper and lower dental arches is as follows: the maxillary arch has the following dentition: front teeth area 31, including upper front teeth 311, upper front teeth 312, upper canine 313;

upper molar area 32, including first premolar 321, second premolar 322, first molar 323, second molar 324 (and the third molar).

The mandibular arch has the following dentition:

front teeth area 41, including lower front teeth 411, lower side front teeth 412, lower canine 413;

The lower molar area 42 includes first premolar 421, second premolar 422, first molar 423, second molar 424 (and the third molar).

The above description is a specific description of a feasible embodiment of the present invention, but this embodiment is not intended to limit the patent scope of the present invention. Any equivalent implementation or modification that does not depart from the technical spirit of the present invention shall be included within the scope of the patent in this case.

Figure 5:
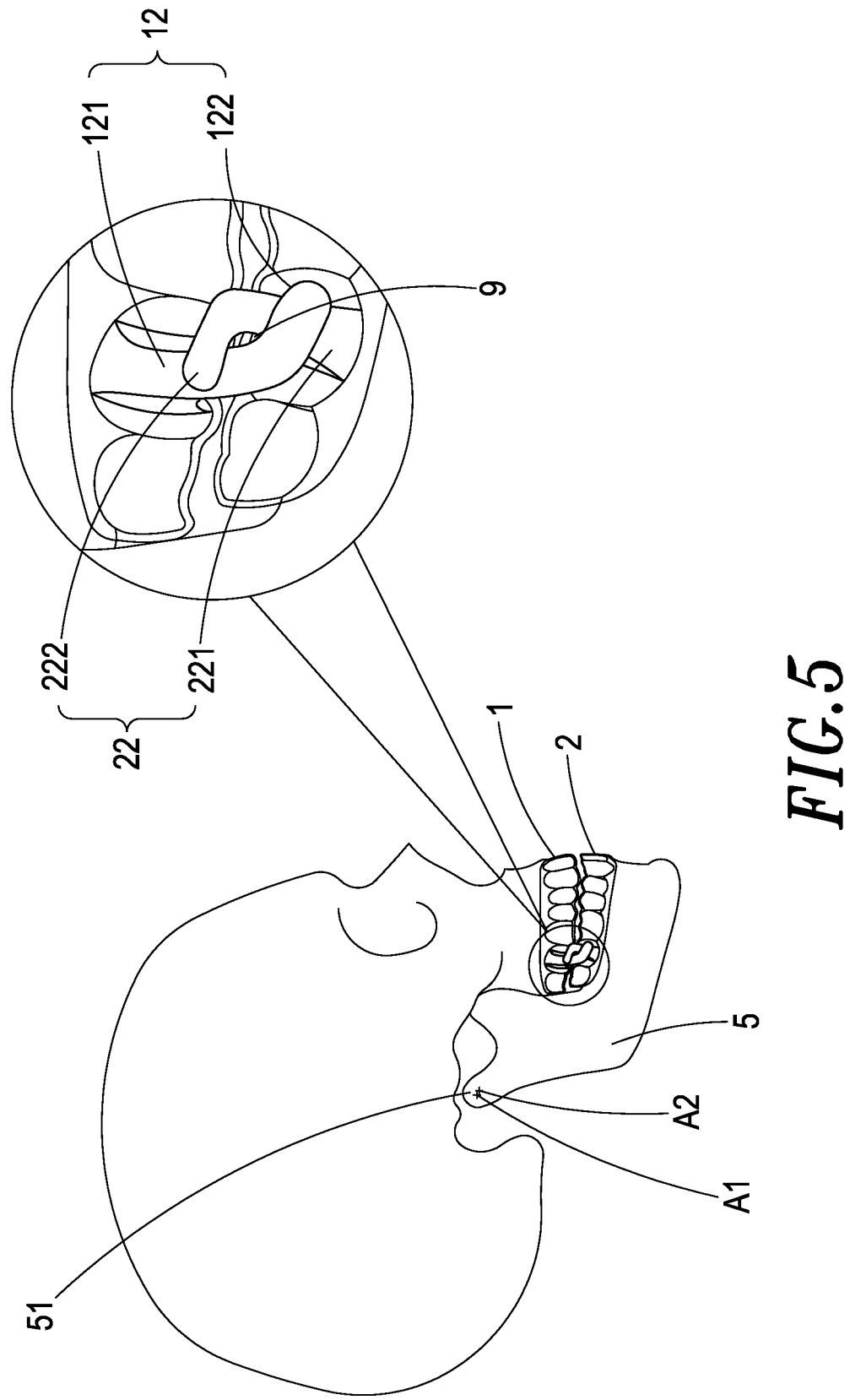
FIG. 5 is the skeletal schematic diagram of the wearing state of the mandible displacement adjusting device of the present invention.
Figure 6:
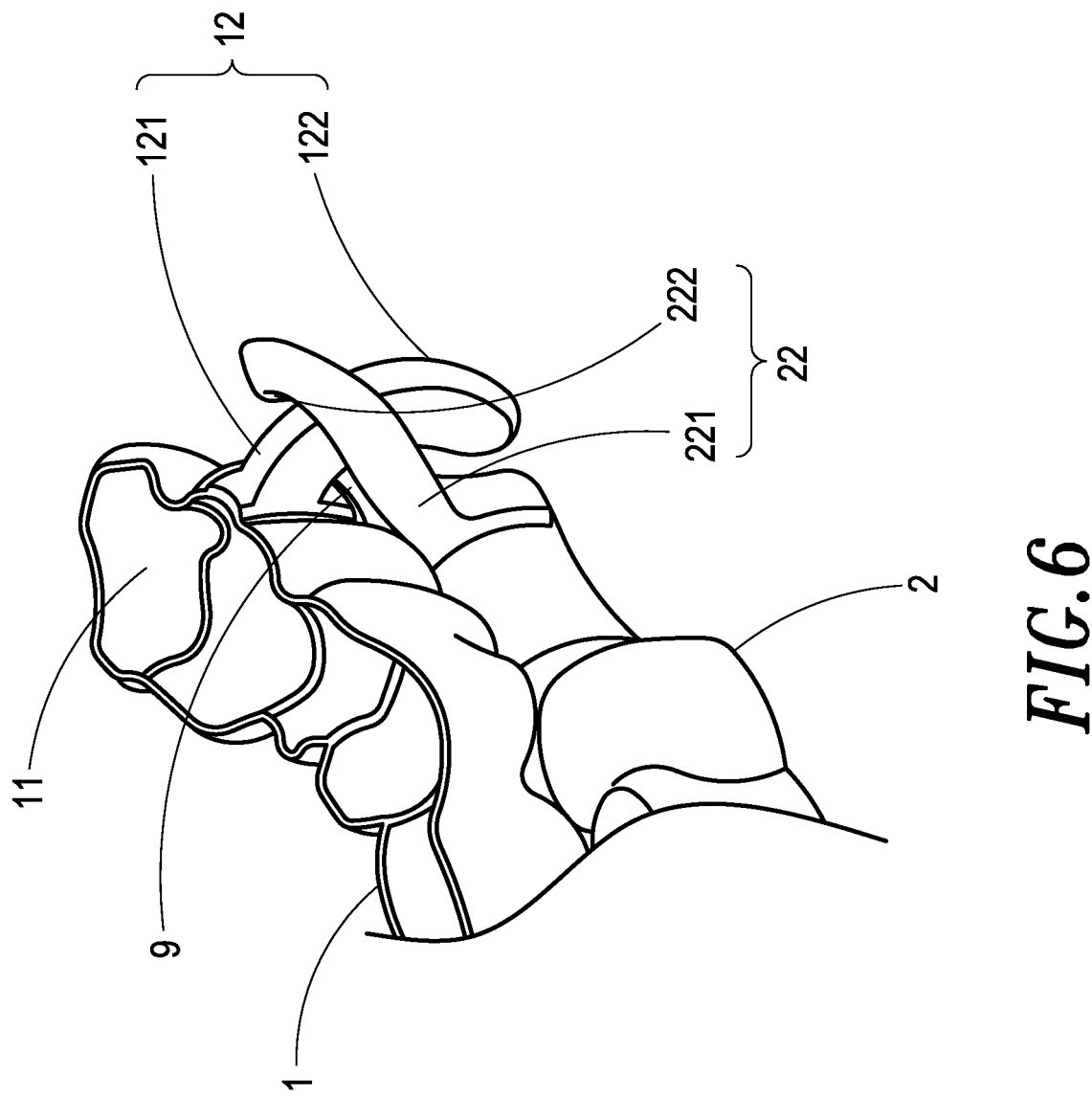
FIG. 6 is a schematic diagram of the connection between the upper braces and the lower braces of the mandible displacement adjusting device of the present invention.
Figure 7:
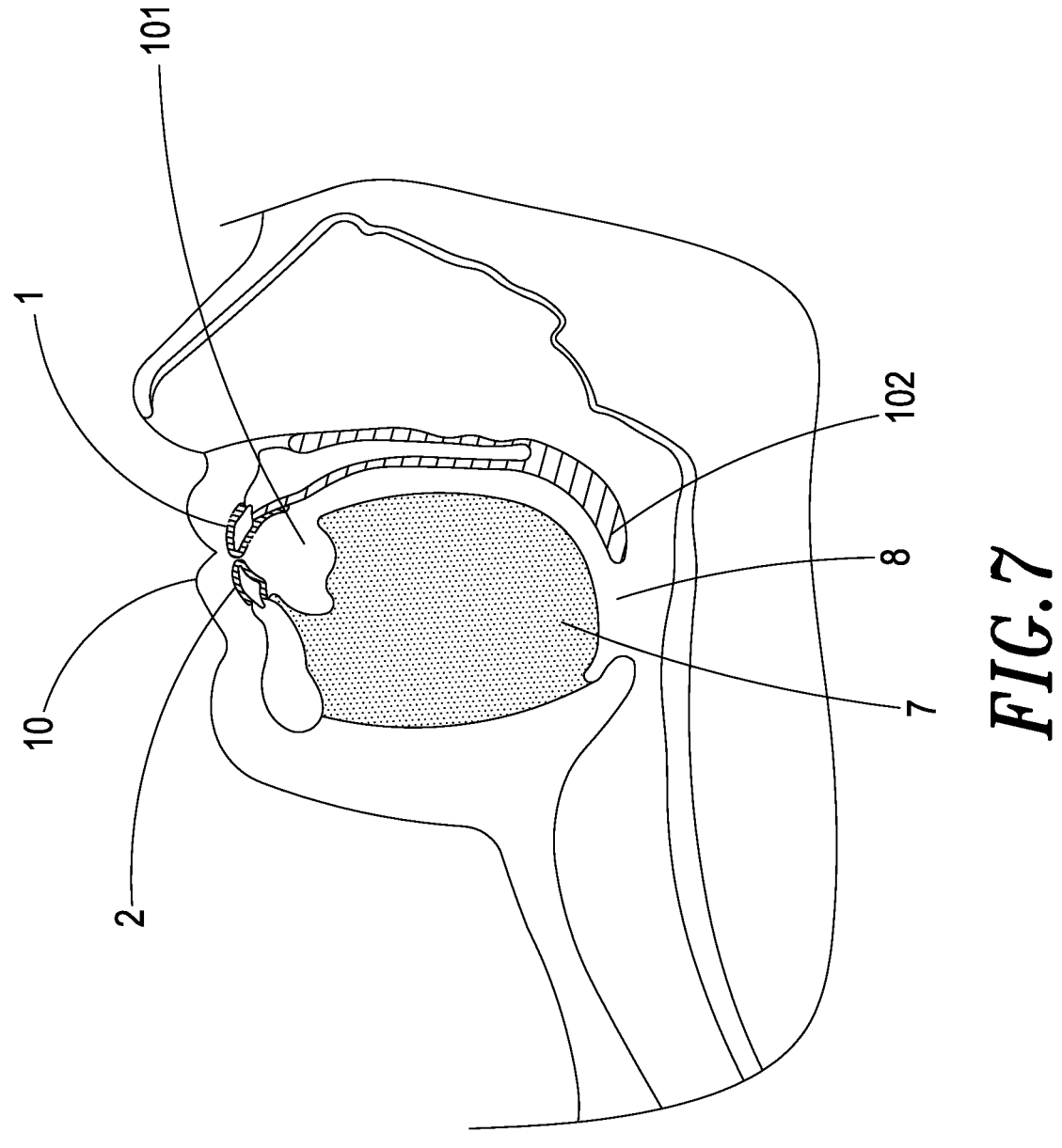
FIG. 7 is a schematic diagram of the breathing passage state after wearing of the mandible displacement adjusting device of the present invention.

As shown in FIG. 3A, FIG. 3B, FIG. 4A, and FIG. 4B, the mandible displacement adjustment device of the present invention includes an upper braces 1 and a lower braces 2, because the upper braces 1 and the lower braces 2 have an upper teeth accommodation space respectively 11 and a lower teeth accommodation space 21. Since the upper braces 1 and the lower braces 2 are made by 3D scanning the user's tooth shape, the upper and lower teeth arches of the human body will be aligned with the upper teeth accommodation space 11 Closely fit with lower teeth accommodation space 21;

The side wall of the upper braces 1 is provided with a first positioning part 12 corresponding to the upper molar area 32, the first positioning part 12 includes a first extension part 121 extending toward the lower molar area 42, and the front end of the first extension part 121 faces the front teeth area 41 bending to form a first hook 122;

The side wall of the lower braces 2 is provided with a second positioning part 22 corresponding to the lower molar area 32, and the second positioning part 22 extends a second extension part 221 toward the upper molar area 32, and the front end of the second extension part 221 faces the condyle 51 of the mandible 5 bends extend a second hook 222;

The first positioning part 12 and the second positioning part 22 are a C-shaped structure or an L-shaped structure that can be movably engaged. Therefore, when wearing the upper braces 1 and the lower braces 2 (the condyle 51 of the mandible 5 is located in the original location A1), the user must control the mandible 5 to move down through the mouth muscles, and then move the mandible 5 forward, driving the lower braces 2 to move forward, and then close the mouth, as shown in FIG. 5, the second Hook 222 will naturally hook back on the first hook 122 (condyle 51 moves to move forward position A2, and the state of hooking is shown in FIG. 6), and in this embodiment, the first positioning part 12 and the second The positioning part 22 is all set to correspond to the side of the first molar 323 periphery. When the first hook 122 is engaged with the second hook 222, the first extension part 121 is mainly used to prevent the second extension part 221 from moving backward, so as to position the mandible 5 at a preset move forward position, which can be tailor-made for the user, take a move forward position that is acceptable to the user's physiological function, and will not cause discomfort due to too much displacement, and the displacement of the mandible 5 depends on the setting of the first positioning part 12 of the upper molar area 32, when the second extension part 221 is blocked by the first extension part 121, can prevent the mandible 5 from moving back to the initial position; in addition, the first hook 122 mainly prevents the second hook 222 from moving down, so that the mandible 5 cannot move downwards, so that the user can avoid opening the mouth during sleep; therefore, when the mandible 5 moves forward and cannot move down to open the mouth, the tongue root 7 and support soft palate 102 can be placed pull it up to keep the breathing passage 8 unblocked during sleep, and avoid apnea and snoring.

In addition, when most people close their mouths, the upper molar area 32 and the lower molar area 42 are mutually occlusal. While the front teeth area 41 is located in the upper anterior tooth area, and when the mandible 5 moves forward to make the front teeth area 31, 41 occluded, a gap is created between the upper molar area 32 and the lower molar area 42.

Figure 8:
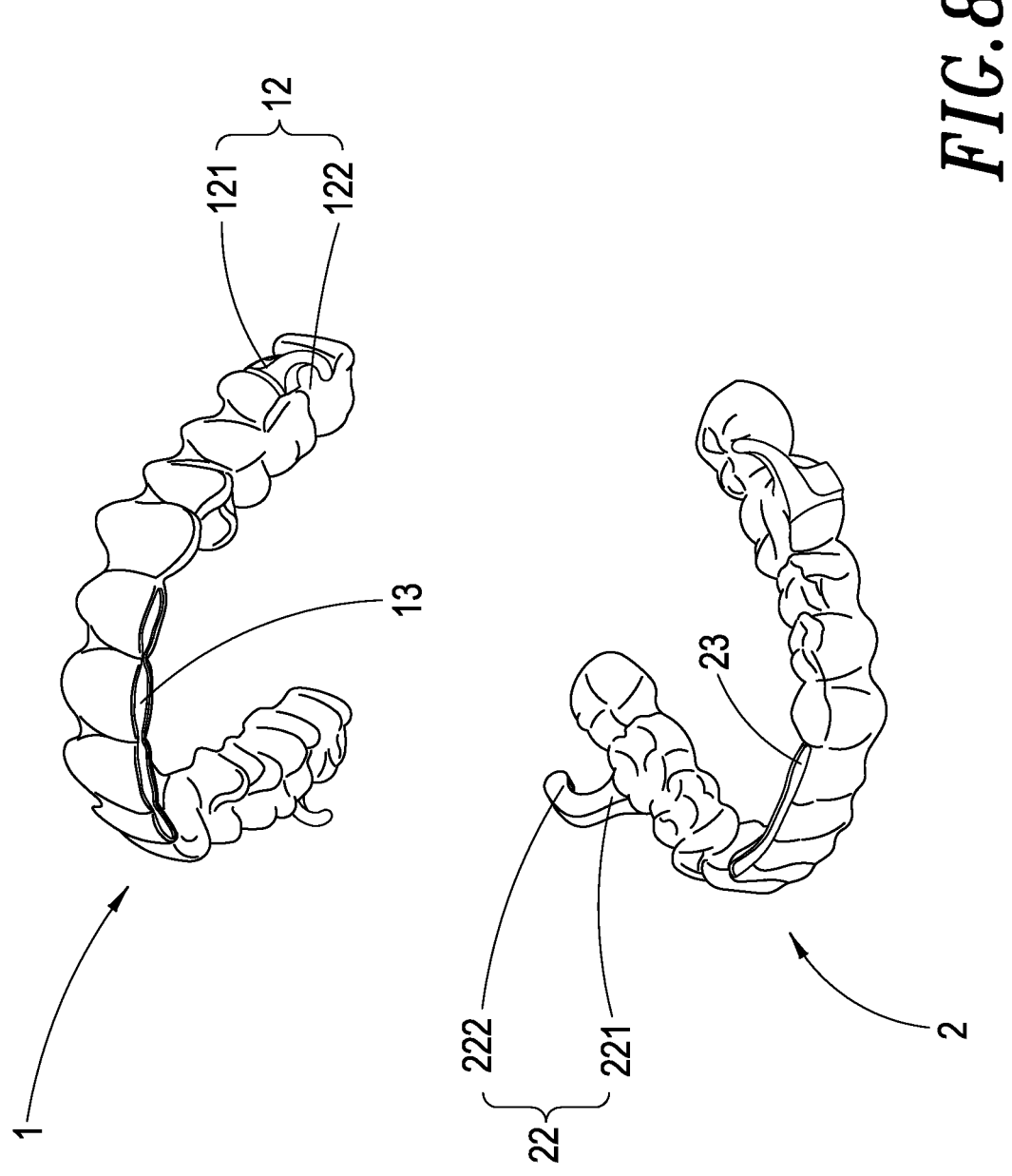
FIG. 8 is a schematic view of the opening structure of the upper braces and the lower braces of the mandible displacement adjusting device of the present invention.

As shown in FIG. 8, the upper braces 1 and/or the lower braces 2 are respectively provided with an opening 13, 23 corresponding the front teeth area 31, 41 of the maxillary dental arch 3 and the mandibular dental arch 4, so as the tooth surfaces of the front teeth area 31, 41 are exposed. When the user's mandible 5 is moved forward, the tooth surfaces of the front teeth area 31, 41 can contact each other, and the upper braces 1 and the lower braces 2 are located on the upper molars. The total thickness of the upper molar area 32 and the lower molar area 42 is smaller than the gap generated between the upper molar area 32 and the lower molar area 42. Therefore, the thickness of the upper braces 1 and/or the lower braces 2 would not be too thick to cause the mandible 5 in a shift position, and causes the discomfort at the condyle 51.

In addition, in order to avoid the user's occlusal discomfort caused by the thickness of the upper braces 1 and/or the lower braces 2, it is possible to adjust the upper braces 1 and the lower braces 2 relative to the upper and lower dental arches of the human body. The thickness of the occlusal surface of the front teeth area 31, 41 is designed to be less than 1 mm, and the combined thickness of upper braces 1 and lower braces 2 located in the upper molar area 32 and lower molar area 42 is less than that between the upper molar area 32 and lower molar area 42 The resulting gap can make the occlusion of the front teeth areas 31 and 41 as similar as possible to the occlusal habit before wearing the braces, so as to reduce the discomfort of the user.

In addition, the first extension part 121 of the first positioning part 12 and the second extension part 221 of the second positioning part 22 extend obliquely at 35-55 degrees, and the extension at an angle of 45 degrees is the best.

Figure 9:
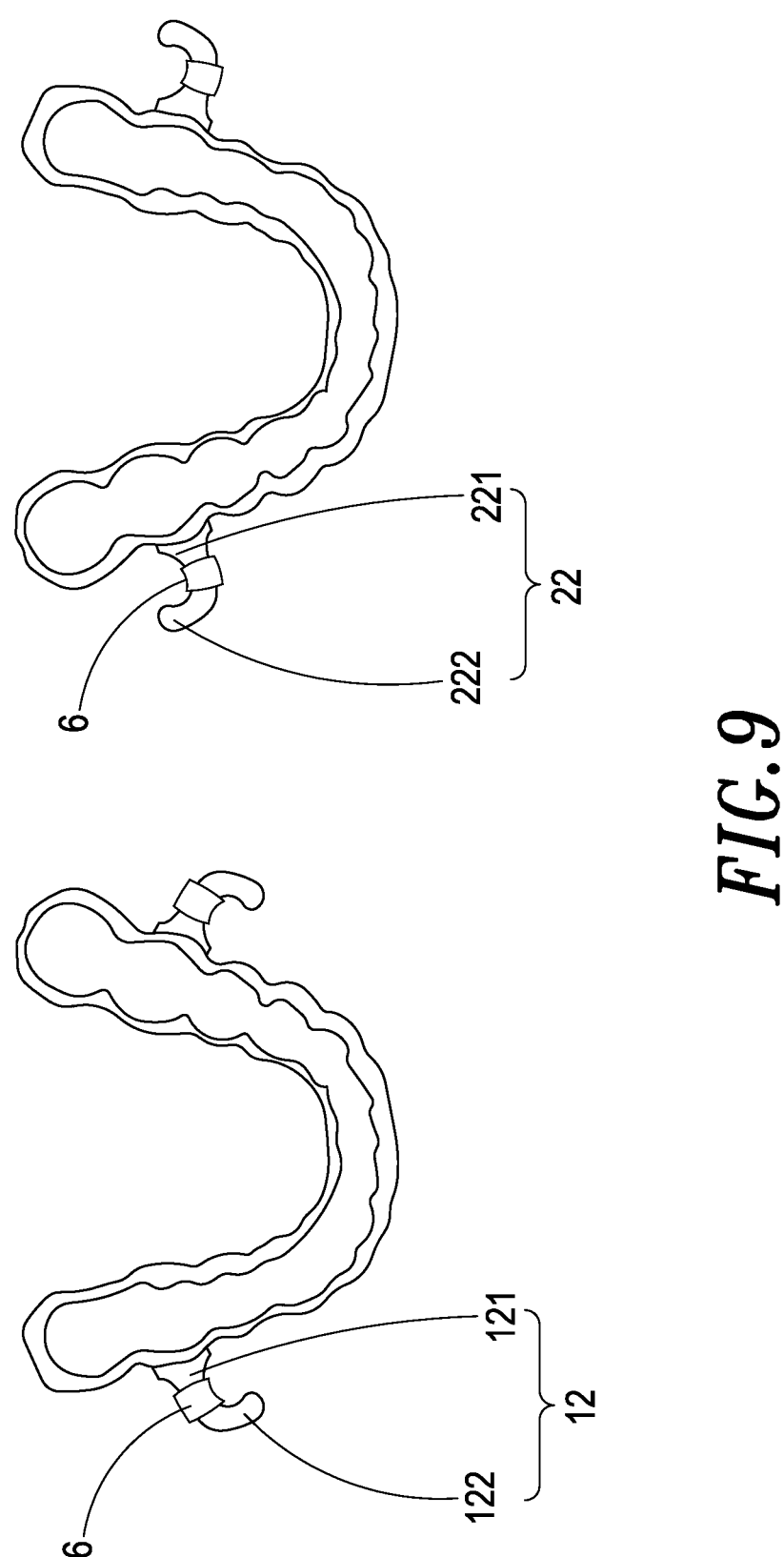
FIG. 9 is a schematic diagram of a sleeve adjuster of the mandible displacement adjusting device of the present invention.
Figure 10C:
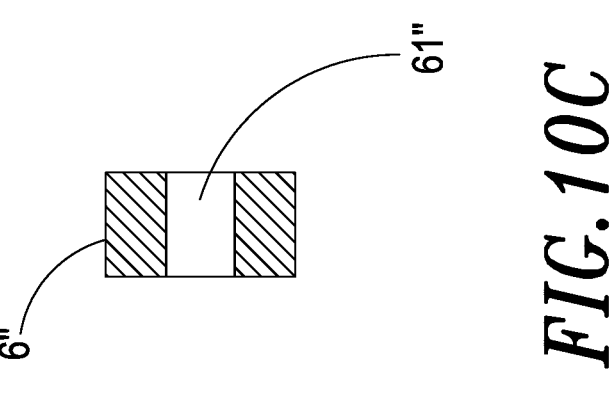
FIGS. 10A-10C are schematic views of the adjuster of the mandible displacement adjusting device of the present invention.
Figure 10B:
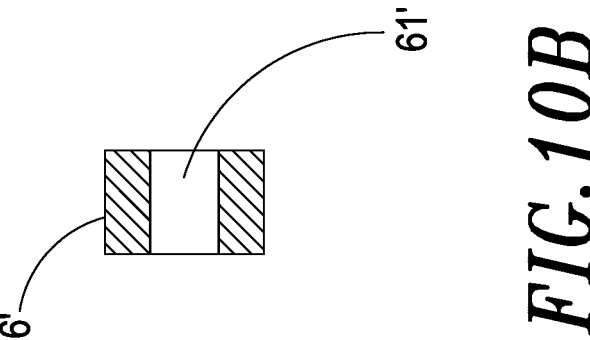
Figure 10A:
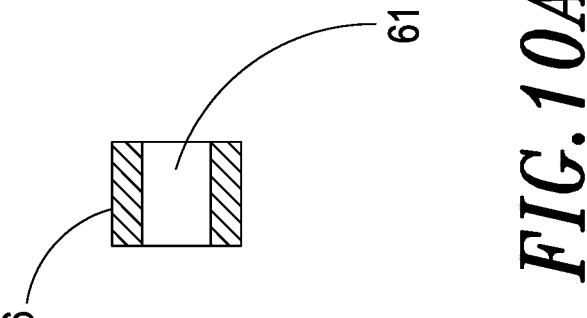

Please refer to FIG. 7, FIG. 9 and FIG. 10A-FIG. 10C, in which, in order to prevent the mandible 5 from moving forward to keep the breathing passage unblocked during sleep, the first extension part 121 or the second extension part 221 can be based on It is required to install an adjuster 6 (as shown in FIG. 9), through the thickness of the adjuster 6, 6', 6", you can control the forward positioning position of the mandible 5. As shown in FIG. 10A-10C, the adjuster 6, 6', 6" are elastic and have a hole 61, 61', 61", through the design of the hole 61, 61', 61", the adjuster 6, 6', 6" is sleeved on the first extension part 121 or On the second extension part 221, the adjuster 6,6',6" can be designed into different thicknesses for users to choose the required adjuster 6,6',6" and adjust the mandible by themselves 5. Move the positioning position forward to achieve the purpose of microadjustment. At the same time, under the move forward position acceptable to the user, keep the breathing passage 8 unblocked, avoid breathing interruption during sleep and achieve the purpose of stopping snoring.

When the mandible displacement adjusting device provided by the present invention is compared with other prior art, its advantages are as follows:

When the human body is sleeping, the mandible 5 can move freely. If the mandible 5 is fixed, after a long time, the condyle 51 of the mandible 5 will definitely produce a great sense of discomfort, and the present invention uses the first positioning part 12 And the second positioning part 22 are both C-shaped or L-shaped structures, so that the first extension part 121 of the first positioning part 12 and the inner space of the first hook 122 form an omnidirectional activity space 9 for the second positioning part 22 The second extension 221 and the second hook 222 can move freely in the omnidirectional activity space 9, therefore, the mandible 5 can move freely in all directions when the user sleeps, and the mandible 5 can move freely when worn for a long time. The condyle 51 of jaw 5 does not produce any discomfort.

When the present invention moves the mandible 5 forward for positioning, the tongue root 7 and the support soft palate 102 will be pulled upward at the same time to keep the breathing passage 8 unobstructed, so as to solve the problem of breathing interruption and snoring of the user during sleep.

The present invention has been disclosed above through the above-mentioned embodiments, but it is not intended to limit the present invention. Anyone who is familiar with this technical field has common knowledge and understands the above-mentioned technical characteristics and embodiments of the present invention without departing from the spirit of the present invention. Within the scope and scope, some changes and modifications can be made, so the patent protection scope of the present invention must be defined according to the appended claims of this specification.

The invention claimed is:

1. A mandible displacement adjustment device, comprising:

an upper braces, having an upper teeth accommodation space formed according to a shape of teeth to fit on a maxilla of a human body, wherein on a side wall of the upper braces extends a first positioning part configured to correspond to an upper molar area, the first positioning part having a first extension part extending from a buccal surface of the side wall of the upper braces and configured to extend obliquely at 35-55 degrees toward a lower molar area, and a front end of the first extension part configured to face a front teeth area bending to form a first hook;

a lower braces, having a lower teeth accommodation space formed according to the shape of the teeth to fit on a mandibular dental arch of the human body, wherein on a side wall of the lower braces extends out a second positioning part configured to correspond to a lower molar area, the second positioning part having a second extension part extending from a buccal surface of the side wall of the lower braces and configured to extend obliquely at 35-55 degrees toward the upper molar area, and a front end of the second extension part is configured to face a condyle of the mandible to form a second hook;

wherein the first positioning part and the second positioning part extending from the buccal surfaces of the upper braces and the lower braces, respectively, allow the upper braces and the lower braces to meet and contact each other;

wherein the first positioning part and the second positioning part are a C-shaped structure that can be movably engaged;

wherein after the upper braces and the lower braces are worn, the first hook is driven to engage with the second hook to form an X-shaped crossing, so that the mandible of the human body is configured to be moved forward and positioned, and the 35-55 degree extension of the first and second extension parts creates an omnidirectional activity space for the second extension part and the second hook moving freely in the omnidirectional activity space between the engaged first hook and second hook, configured to let the mandible move freely to avoid discomfort due to wearing at a condyle of the mandible for a long time;

wherein the second extension part of the second positioning part is blocked by the first extension part of the first positioning part and is unable to move backward at a blocking position when moving backward in a horizontal direction, and the blocking position is a preset position for mandible forward positioning, when a mouth of the human body is closed, the first hook of the first positioning part and the second hook of the second positioning part are configured to engage with each other, and when the mandible moves downward, the second hook is configured to be blocked by the first hook to keep the mouth of the human body closed.

2. The mandible displacement adjustment device of claim 1, wherein both the upper molar area and the lower molar area each are configured to include a first premolar, a second premolar, a first molar, a second molar, and include a first premolar, a second premolar, a first molar, a second molar, and positions of the first positioning part and the second positioning part are configured to correspond to one side of either of the second molar and the first molar, or between any two molars.

3. The mandible displacement adjustment device of claim 2, wherein a preferred position of the first positioning part and the second positioning part correspond to a side of the first molar.

4. The mandible displacement adjustment device of claim 3, wherein the first positioning part is positioned on the position of the upper molar area, which is a preset position of mandible forward positioning, the position of the first positioning part configured to be located in the upper molar area is tailored according to an acceptable position of the mandible forward positioning, so that the mandible will not generate discomfort when the mandible is positioned forward.

5. The mandible displacement adjustment device of claim 1, wherein the upper braces or/and the lower braces are provided with an opening corresponding to a front teeth area of a human maxillary dental arch or/and the mandibular dental arch of the human body, so as to expose a tooth surface of the front teeth area.

6. The mandible displacement adjustment device of claim 1, wherein a thickness of the upper braces and the lower braces corresponding to a front teeth area of a human maxillary dental arch and the mandibular dental arch of the human body is less than 1 mm.

7. The mandible displacement adjustment device of claim 1, wherein the first extension part of the first positioning part or the second extension part of the second positioning part is set with an adjuster, a thickness of the adjuster is used to finely adjust a position of the mandible forward positioning.

* * * * *